United States Patent [19]

Clark, Jr.

[11] 3,937,813

[45] Feb. 10, 1976

[54] **INSECTICIDAL COMPOSITIONS COMPRISING MIXTURES OF *BACILLUS THURINGIENSIS* AND CHLORDIMEFORM**

[75] Inventor: Robert Kingsbury Clark, Jr., St. Petersburg, Fla.

[73] Assignee: Abbott Laboratories, North Chicago, Ill.

[22] Filed: Feb. 20, 1974

[21] Appl. No.: 444,076

[52] U.S. Cl. ............................. 424/93; 424/326
[51] Int. Cl.$^2$. A01N 9/02; A01N 9/20; A01N 15/00
[58] Field of Search ........................... 424/93, 326

[56] References Cited
OTHER PUBLICATIONS

Harris et al., J. Econ. Entomol., 1970, 63, pp. 666–667.

*Primary Examiner*—Stanley J. Friedman
*Assistant Examiner*—Allen J. Robinson
*Attorney, Agent, or Firm*—Robert L. Niblack; Vincent A. Mallare

[57] ABSTRACT

Compositions for inhibiting the growth of lepidopterous larvae on plants comprising mixture of *Bacillus thuringiensis* and N'-(4-chloro-o-tolyl)-N,N-dimethyl formamidine (Chlordimeform) having the structure

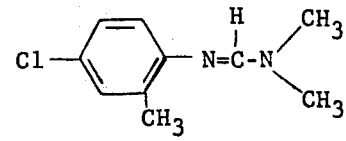

6 Claims, No Drawings

INSECTICIDAL COMPOSITIONS COMPRISING MIXTURES OF *BACILLUS THURINGIENSIS* AND CHLORDIMEFORM

BACKGROUND OF THE INVENTION

This invention relates to insecticides, but more particularly, it relates to a combination of insecticides which is effective in controlling the growth of various lepidopterous larvae on various crops and in controlling the damage from such larvae.

In the control of various lepidopterous larvae, there have been provided several insecticides, which have at least in part been effective in the control of the growth thereof. Under normal conditions, or under ideal environmental conditions, larvae feed and grow rapidly within a short period of time. Thus, economic crops or ornamental plants left untreated are fully available for the various forms of insect larvae to consume and damage.

Many chemical insecticides which are useful in controlling insects on economic crops do not control well the insect larvae belonging to the order Lepidoptera. Some offer minimal control or control of only early or later growth stages (instars) of the said larvae. Further, during the course of use, said larvae may become resistant to minimal levels of insecticide. In both instances, larger quantities may be used without added benefit, but with added cost and environmental contamination.

Attempts have been made and some practices adopted to develop and use separate applications of insecticides to provide broader control of injurious and economically important lepidopterous larvae and other insects. In some combinations, the beneficial effects of such insecticides has been partial and unspecific. Again, large quantities of chemical insecticide combinations may be necessary, adding to cost and environmental problems.

Therefore, it is the primary purpose of the present invention to provide an effective and yet practical insecticide combination which can control not only the first but also later instars (growth stages) of various lepidopterous larvae that feed on various vegetable crops, field crops, deciduous fruits and nut crops, shade and forest trees and ornamental flowers, shrubs and the like.

DETAILED DESCRIPTION OF THE INVENTION

This invention provides a combination of at least two insecticides to give a more complete and effective control of the growth of various lepidopterous larvae on various crops. The effect of this combination is to combine and integrate the best properties of the individual insecticides such as an environmentally compatable biological insecticide and reduced amounts of chemical insecticide to provide economic control of a spectrum of larval stages of the various lepidopterous larvae.

The combination of insecticide which has proven most effective in the control of such lepidopterous larvae is the biological insecticide, *Bacillus thuringiensis* (B.t.) and the chemical insecticide, N'-(4-chloro-o-tolyl)-N,N-dimethylformamidine (chlordimeform).

In the control of the various lepidopterous larvae, *Bacillus thuringiensis* (B.t.) is a naturally occuring biological insecticide, environmentally safe, highly specific, and effective as a stomach poison only for lepidopterous larvae. *Bacillus thuringiensis* causes immediate cessation of feeding and causes subsequent death of said larvae. That is, newly hatched or developing insect larvae feeding on any plant treated with *Bacillus thuringiensis* insecticide (for simplification and clarification herein after referred to as B.t.,) will succumb to the specific biological mechanisms provided thereby.

According to the present invention, growth of the larvae is effectively controlled by a combination of B.t. insecticide and the chemical chlordimeform insecticide. The chlordimeform is effective in controlling small larvae, but it also has ovicidal properties.

The combined and integrated properties of the B.t. insecticide and the chlordimeform insecticide provide more effective and longer control of the growth of such lepidopterous larvae at low rates of each component. Also, the rate of the chlordimeform may stress the insect, and under these conditions, the activity of the B.t. insecticide is apparently more pronounced. Thus, the combination of mixtures appear to be synergistic in effect. By different use of such combinations or mixtures, the synergistic effect is substantiated in the effective and practical control of such lepidopterous larvae.

The combinations of insecticides of the present invention is made quite simply in that different amounts and proportions of the individual insecticide are mixed together to provide an effective and economical application. For example, B.t. is mixed with chlordimeform, N'-(4-chloro-o-tolyl)-N,N-dimethylformamidine, and the combination added to water in a spray tank or each component may be added to water and mixed together. The two insecticides may be mixed with each other in different proportions, for example, the B.t. and chlordimeform may be in equal parts or in a proportion where there is more B.t. than chlordimeform, or conversely where there is more chlordimeform than B.t. For example, there may be 0.25 lbs. per acre of B.t., and 0.125 lbs. per acre of chlordimeform, or 0.25 lbs. per acre of chlordimeform and 0.125 lbs. per acre of B.t. The combination which has been found to be generally most advantageous, is a mixture of equal proportions of both the B.t. and the chlordimeform. For example, this would be one-eighth to one-half lb. per acre of each of the B.t. and chlordimeform.

The following examples will further illustrate the present invention and its advantages in the treatment and control of various lepidopterous larvae.

EXAMPLE 1

A series of tests were made to compare B.t. and N'-(4-chloro-o-tolyl)-N,N-dimethylformamidine, and combinations thereof, for control of the cabbage looper (*Trichoplusia ni*), and the fall armyworm (*Spodoptera frugiperda*) and the imported cabbage worm (*Pieris rapae*) on fall cabbage. In this test, B.t. wettable powder was applied at 2.0 lbs. per acre, was compared with B.t. and the chlordimeform at one-eighth and one-sixteenth lb. per acre, applied alone and in combination. In the round Dutch cabbage that was treated, was a moderate infestation of the cabbage looper and a very light infestation of imported cabbage worm and fall armyworm. Similar rows of 3 feet by 50 feet were arranged in a random design. Each treatment was replicated five times. The insecticidal spray was applied with a hand pressure sprayer delivering 50 gallons per acre and Triton B-1956 spreader-sticker, was added at the rate of 4 ml. per gallon of the final spray. Seven applications of the combined insecticide were made in a six week period. During the growing season, three weekly larval counts were made. At the harvest, treatments were graded as follows:
  Class 1 - no visible feeding to the head or wrapper leaves;
  Class 3 - four or more wrapper leaves damaged.

Results of the tests are provided in Table I below. The results as provided, show the average number of surviving larvae and pupae per 100 plants, as provided by the application of the different insecticides and combinations thereof. Also, the grades of the resultant plant are provided.

TABLE I

| Material | Dosage/Acre (lb) | Average per 100 plants of surviving larvae and pupae | | | % Plants in | |
|---|---|---|---|---|---|---|
| | | Cabbage looper | Fall armyworm | Imported cabbageworm | Class 1 | Class 3 |
| B.t.[1] | 0.125 | 17 | 2 | 0 | 60 | 8 |
| Chlordimeform[2] | 0.125 | 41 | 0 | 2 | 30 | 16 |
| B.t. + Chlordimeform | 0.125 + 0.125 | 5 | 0 | 1 | 88 | 0 |
| B.t. | 0.0625 | 23 | 0 | 0 | 45 | 9 |
| Chlordimeform | 0.0625 | 17 | 0 | 1 | 51 | 7 |
| B.t. + Chlordimeform | 0.0625 + 0.0625 | 16 | 0 | 0 | 89 | 0 |
| B.t. | 2.0 | 2 | 0 | 0 | 90 | 0 |
| Untreated | | 93 | 8 | 6 | 8 | 46 |

[1]Source DIPEL WP (brand name of *Bacillus thuringiensis* 16,000 International Units (IU) per milligram or 7.26 Billion International Units (BIU) of potency per pound from Abbott Laboratories.
[2]Source FUNDAL (brand name of chlordimeform from Schering A. G. (Berline/Bergkamon) and Nor-AM (USA)

As shown in Table I, the combinations of B.t. and chlordimeform of the present invention at one-eighth and one-sixteenth lb/acre was equal to B.t. alone at 2 lb/acre. Also, as shown, the combination of B.t. and chlordimeform at one-sixteenth lb/acre was superior to either product used alone at one-eighth lb/acre when a number of marketable heads was measured. In this test, it clearly appears that the combination of the B.t. and chlordimeform have a synergistic reaction, in that the combination produces a superior result over either of the insecticides alone.

EXAMPLE 2

A similar test to that of Example 1 was performed to compare various insecticides and combinations thereof, including B.t., for control of the cabbage looper (*Trichoplusia ni*), the Diamondback moth (*Plutella maculipennis*) and the imported cabbage worm (*Pieris rapae*) on spring cabbage. In the test, B.t. and two chlordimeform sources were applied separately at low rates and in combination. Single rows of round Dutch cabbage, 3 feet by 50 feet, were arranged in a random design. Each treatment was replicated 5 times. The sprays were applied by a hand operated pressure sprayer at a rate of 50 gallons per acre. Six weekly applications were made over a six week period, and Triton B-1956 spreader-sticker was added to each spray at the rate of 4 ml. per gallon.

Four weekly larval counts were made. Each replicate was assessed as to the marketability as follows:
  Class 1 - minimal feeding to the outer leaves;
  Class 2 - damage to the outer leaves, but no injury to the head; and
  Class 3 - injury and damage to the head.

The results of the tests are provided below, in Table II:

TABLE II

| Material | Dosage/Acre (lb) | Cabbage looper | Percent reduction | Diamondback moth | Percent reduction | Imported cabbageworm | Percent reduction | % Plants in Class 1 | Class 2 |
|---|---|---|---|---|---|---|---|---|---|
| B.t.[1] | 0.25 | 33 | 51 | 2 | 80 | 1 | 98 | 37 | 10 |
| Chlordimeform A[2] | 0.25 | 7 | 89 | 1 | 90 | 14 | 79 | 10 | 41 |
| Chlordimeform B[3] | 0.25 | 7 | 89 | 1 | 90 | 16 | 76 | 13 | 35 |
| B.t. + Chlordimeform A | 0.25 + 0.25 | 3 | 95 | 0 | 100 | 0 | 100 | 87 | 1 |
| B.t. + Chlordimeform B | 0.25 + 0.25 | 5 | 92 | 1 | 90 | 2 | 97 | 85 | 2 |
| B.t. | 0.125 | 23 | 66 | 1 | 90 | 2 | 97 | 24 | 17 |
| Chlordimeform A | 0.125 | 4 | 94 | 1 | 90 | 12 | 82 | 13 | 34 |
| B.t. + Chlordimeform A | 0.125 + 0.125 | 1 | 98 | 0 | 100 | 0 | 100 | 91 | 1 |
| Untreated | | 67 | | 10 | | 67 | | 0 | 90 |

[1]DIPEL WP, brand name of *Bacillus Thuringiensis* 16,000 IU/mg(7.26 BIU per lb) from Abbott Laboratories
[2]FUNDAL, brand name of chlordimeform from Schering A. G. (Berlim/Bergkamen) and Nor-Am (USA)
[3]GALECRON, brand name of chlordimeform from CIBA-Geigy As shown in Table II, B.t. was applied at 0.125 and 0.25 lb./acre and chlordimeform A was applied at the same rates, whereas chlordimeform B, a similar formulation of chlordimeform, was applied at 0.25 lb./acre. Also, as shown in the results of Table II, the combination of 0.125 lb. of chlordimeform A and 0.125 lb. of B.t. was superior in marketable heads when compared to B.t., chlordimeform A or chlordimeform B as a single spray at 0.25 lb./acre. The results of this test clearly indicate a synergistic action of the combination of B.t. with the chlordimeform insecticides.

EXAMPLE 3

A series of tests were made on Fall collards to compare B.t. and chlordimeform alone and in combination for control of the cabbage looper (*Trichopulsia ni*) and the Fall armyworm (*Spodoptera frugiperda*).

In these tests, B.t. was applied at 0.25, 0.5, and 2.0 lb./acre, whereas chlordimeform was applied at 0.25 and 0.5 lb./acre. A combination of B.t. and chlordimeform were applied at 0.25 and 0.5 of each insecticide per acre. The collards were arranged in a random block design of single rows, 3 feet by 50 feet. Each treatment was replicated five times. The insecticide sprays were applied by a hand pressure sprayer delivering 50 gallons per acre. Triton B-1956 was used as a spreader-sticker at the rate of 4 ml. per gallon of final spray. Seven applications were made at weekly intervals over a period of six weeks. During the test, three separate larval counts were taken and averaged. At harvest, five plants from each replicate were examined for injured leaves. The results of the test are provided below, in Table III.

The results of the test are provided below in Table IV.

TABLE IV

| Material | Amt./Acre (lb) | Damage Scores 6 Days Post-Ap. | 13 Days Post-Ap. |
|---|---|---|---|
| B.t.[1] | 0.5 | 2.11 | 1.90 |
|  | 1 | 2.01 | 1.86 |
| Chlordimeform[2] | 1 | 1.68 | 1.38 |
|  | 0.25 | 1.75 | 1.24 |
|  | 0.5 | 2.09 | 1.44 |
| B.t. + | 0.5 + 0.25 | 1.56 | 1.12 |

TABLE III

| Material | Dosage/Acre (lb) | Average per 100 plants of surviving larvae and pupae | | | | Percent plants with this many leaves injured | | | | Percent injured plants |
|---|---|---|---|---|---|---|---|---|---|---|
| | | Cabbage looper | Percent reduction | Fall Army-worm | Percent reduction | 0 | 1 | 2–10 | 10+ | |
| B.t.[1] | 0.5 | 18 | 78 | 2 | 67 | 88 | 7 | 5 | 0 | 12 |
| Chlordimeform[2] | 0.5 | 11 | 87 | 1 | 83 | 64 | 14 | 22 | 0 | 36 |
| B.t. + Chlordimeform | 0.5 + 0.5 | 5 | 94 | 1 | 83 | 98 | 1 | 1 | 0 | 2 |
| B.t. | 0.25 | 24 | 71 | 1 | 83 | 78 | 8 | 13 | 1 | 22 |
| Chlordimeform | 0.25 | 15 | 82 | 0 | 100 | 75 | 7 | 17 | 1 | 25 |
| B.t. + Chlordimeform | 0.25 + 0.25 | 10 | 88 | 0 | 100 | 92 | 4 | 4 | 0 | 8 |
| B.t. | 2.0 | 6 | 93 | 0 | 100 | 95 | 5 | 0 | 0 | 5 |
| Untreated | — | 82 | — | 6 | — | 12 | 9 | 70 | 9 | 88 |

[1] DIPEL WP, brand name of *Bacillus thuringiensis* 16,000 IU/mg (7.26 BIU per lb) from Abbott Laboratories
[2] FUNDAL brand name of chlordimeform from Schering A. G. (Berlin/Bergkmon) or Nor-Am (USA)

As shown in the Table, the combination of B.t. and chlordimeform at the low rate of 0.25 lb./acre provided greater control than chlordimeform used alone at 0.5 lb./acre, and at least equal the control provided by B.t. at 0.5 lb./acre when determining the plant injury. Also, as shown in the Table, the best protection for the collard plants was provided by the application of B.t. alone at 2.0 and 0.5 lb./acre, and the combination of B.t. and chlordimeform at 0.5 and 0.25 lb./acre. This effectiveness of the combination of B.t. and chlordimeform shows that such combination has a synergistic action.

| Chlordimeform | 1 + 0.5 | 0.95 | 0.78 |
|---|---|---|---|
| Untreated | — | 3.78 | 3.80 |

[1] DIPEL WP, brand name of *Bacillus thuringiensis* 16,000 IU/mg (7.26 BIU per lb) from Abbott Laboratories
[2] FUNDAL, brand name of chlordimeform from Schering A.G. (Berlin/Bergkamon) or Nor-AM (USA)

As shown in Table IV, B.t. at 0.5 and 1.0 lb./acre gave commercial control. However, the combinations of B.t. and chlordimeform were better. As shown in the results provided in Table IV, the combination of B.t. and chlordimeform provide a synergistic action.

EXAMPLE 4

A test was run to compare various insecticides, including B.t. alone and B.t. in combination with chlordimeform for control of cabbage looper (*Trichoplusia ni*) on cabbage. The test was made on plots of 4 rows of 25 plants of market prize cabbage, arranged in a random design. Each treatment was replicated four times. Then the insecticidal sprays were applied by a backpack hand sprayer at rates of 50 and 100 gallons per acre. The sprays were applied over a period of six weeks. The damage ratings were taken on five heads selected at random from each plot, six and 13 days after the last application. The following score was used for such damage, if any.

0 equal to no damage
 1 equal to non-economic damage
 3–5 equal to economic damage to the head

EXAMPLE 5

A series of tests were made on tomatoes to compare B.t. and chlordimeform alone and in combination for control of tomato pinworm (*Keiferia lycopersicella*).

In these tests on tomatoes, in small plots, the tomato pinworm was the most important economic pest. The insecticides individually and in combination were applied by sprays for ten applications over a two-month period. The spray applications were applied by a powdered pressure sprayer at 90 to 125 gallons per acre. From the tests, leaf injury data and yield were determined as shown below in Tables V and VI.

The leaf injuries were taken by examining the top three (3) leaves on two (2) plants in each plot. At each of the four (4) harvests, the total yield from each plot was recorded.

TABLE V

Mean Number of Tomato Pinworm Larval Injuries/3 Top Leaves/2 Plants on Power-Sprayed Plots

| Material | Treatment Amt./100 Gals | Larval Damages/3 Top Leaves/2 Plants on Date Total Count 3 Days | 4/4 ns | 4/18 | 5/1 ns |
|---|---|---|---|---|---|
| B.t.[1] + Chlordimeform[2] | 2 oz. + 2 oz. | 1.75 | .75 | 0.00 a | 1.00 |
| B.t. + Chlordimeform | 4 oz. + 4 oz. | 2.50 | .25 | 0.50 ab | 1.75 |
| Chlordimeform | 8 oz. | 2.75 | 1.00 | 1.00 ab | 0.75 |
| B.t. | ½ lb. | 8.00 | 1.00 | 3.25 ab | 3.75 |

TABLE V-continued

Mean Number of Tomato Pinworm Larval Injuries/3 Top Leaves/2 Plants on Power-Sprayed Plots

| Material | Treatment Amt./100 Gals | Larval Damages/3 Top Leaves/2 Plants on Date | | | |
|---|---|---|---|---|---|
| | | Total Count 3 Days | 4/4 ns | 4/18 | 5/1 ns |
| Untreated | — | 18.25 | 3.75 | 8.25 c | 6.25 |

[1]DIPEL SP, brand name of *Bacillus thuringiensis* 16,000 IU/mg (7.26 BIU per lb) from Abbott Laboratories
[2]FUNDAL, brand name of chlordimeform from Schering A. G. (Berlin/Bergkmon) or Nor-Am (USA)

TABLE VI

| | Mean Number of Fruit/Plot, Four Pickings | |
|---|---|---|
| Material | Treatment Amt./100 Gals. | Mean No. Fruit/Plot |
| B.t.[1] | ½ lb. | 79 |
| Untreated | — | 80 |
| Chlordimeform[2] | ½ lb. | 89 |
| Chlordimeform + B.t. | 4 oz. + 4 oz. | 91 |
| Chlordimeform + B.t. | 2 oz. + 2 oz. | 116 |

[1]DIPEL SP, brand name of *Bacillus thuringiensis* 16,000 IU/mg (7.26 BIU per lb) from Abbott Laboratories
[2]FUNDAL, brand name of chlordimeform from Schering A. G. (Berlin/Bergkmon) or Nor-Am (USA)

As shown in Tables V and VI, B.t. at 0.5 lb/100 gallons gave commercial control of the growth of the tomato pinworm larvae. However, the combination of B.t. and chlordimeform at a lesser quantity (e.g. 2 oz. + 2 oz/100 gals.) gave superior control. As clearly indicated in the results provided in Tables V and VI, the combination of B.t. and chlordimeform provide a synergistic action.

The results provided in the Examples above show that the combination of B.t. with chlordimeform provide a synergistic action which is effective in control of the various types of lepidopterous larvae on various plants. In addition to the plants shown in the Examples, the combination of B.t. with chlordimeform provides control of tomato fruitworm (*Heliothis zea*) on staked tomatoes, and for control of budworm and bollworm (*Heliothis spp*) on cotton. Also, the combination of B.t. with chlordimeform provides control of lepidopterous on other cole plants, leafy vegetables, tobacco, corn and the like. Combination of the B.t. with chlordimeform provides effective control of lepidopterous larvae at lower rates and provides an opportunity for economics and less environmental accumulation of the chemical agent.

The combination insecticide may be utilized in diverse formulations, including the adjuvants and carriers normally employed for facilitating the dispersion of active ingredients for agricultural applications, recognizing a known fact that the dosage, formulation, mode of application of a chemical agent and other variables may affect its activity in any given application. Thus, the just-described B.t. insecticide combination may be formulated as a solution or dispersion, in aqueous or non-aqueous media, as a powdery dust, as a wettable powder, as an emulsifiable concentrate, as a granule, or as any of several other known types of formulations, depending on the desired mode of application. These growth regulatory compositions may be applied as sprays, dips, dust, or granules to the plant situs in which growth regulation of the larvae is desired.

In order to provide compositions in the form of dust, granules, water dispersible powders, aqueous solutions, dispersions, or emulsions and solutions or dispersions in organic liquids, the carrier or diluent agent in such formulations may be a finely divided solid, an organic liquid, water, a wetting agent, a dispersing agent, or emulsifying agent, or any suitable combination of these. Generally, when liquids and wettable powders are prepared a conditioning agent comprising one or more surface-active agents or surfactants is present in amounts sufficient to render a given composition containing the active compounds readily dispersible in water or in oil.

The surface active agent used in the invention here can be a wetting, dispersing or emulsifying agent which will assist dispersion of the compound. The surface-active agent or surfactant can include such anionic, cationic and non-ionic agents as have heretofore been generally employed in plant control compositions of similar type. Suitable surface-active agents are set forth, for example, in "Detergents and Emulsifiers" 1971 Annual by John W. McCutcheon, Inc.

In general, less than 10% by weight of the surface-active agent will be used in compositions of this invention, and ordinarily the amount of surface-active agent will range from 1 – 5% but may even be less than 1% by weight.

Additional surface-active agents can be added to the formulations to increase the ratio of surfactant:active ingredient up to as high as 5:1 by weight. Such compositions may have a greater biological effectiveness than can be expected from a consideration of the activity of the components used separately. When used at higher ratios, it is preferred that the surfactant be present in the range of one-fifth to five parts surfactant for each one part of active agent.

WETTABLE POWDERS

Wettable powders are water-dispersible compositions containing the active material, an inert solid extender, and one or more surfactants to provide rapid wetting and prevent heavy flocculation when suspended in water.

The inert extenders which are preferred for use in the wettable powders of this invention containing the active compounds are of mineral origin.

The classes of extenders suitable for the wettable powder formulations of this invention are the natural clays, diatomaceous earth and synthetic mineral fillers derived from silica and silicate. Most preferred fillers for this invention are kaolinites, attapulgite clay, montmorillonite clays, synthetic silicas, synthetic magnesium silicate and calcium sulfate dihydrate.

Among the more preferred surfactants are the nonionic and anionic types, and those most suitable for the preparation of the dry, wettable products of this invention are solid forms of compounds known to the art as wetters and dispersants. Occasionally a liquid, nonionic compound classified primarily as an emulsifier may serve as both wetter and dispersant.

Most preferred wetting agents are alkylbenzene and alkylnapthalene sulfonates, sulfated fatty alcohols, amines or acid amides, long chain acid esters of sodium isethionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium napthalene sulfonates, polymethylene bisnapthalene sulfonate, and sodium-N-methyl-N-(long chain acid) taurates.

Wetting and dispersing agents in these preferred wettable powder compositions of the invention are usually present at concentrations of from about 0.5 weight percent to 5 weight percent. The inert extender than completed the formulation. Where needed, 0.1 weight percent to 1.0 weight percent of the extender may be replaced by a corrosion inhibitor or an anti-foaming agent or both.

Thus, wettable powder formulations of the invention will contain from about 25 to 90 weight percent active material, from 0.5 to 2.0 percent wetting agent, from 0.25 to 5.0 weight percent dispersant, and from 9.25 to 74.25 weight percent inert extender, as these terms are described above.

When the wettable powder contains a corrosion inhibitor or an anti-foaming agent or both, the corrosion inhibitor will not exceed about 1 percent of the composition, and the anti-foaming agent will not exceed about 0.5 percent by weight of the composition, both replacing equivalent amounts of the inert extender.

DUSTS

Dusts are dense powder compositions which are intended for application in dry form. Dusts are characterized by their free-flowing and rapid settling properties so that they are not readily windborn to areas where their presence is not desired. They contain primarily an active ingredient and a dense, free-flowing, solid extender. Their performance is sometimes aided by the inclusion of a wetting agent, and convenience in manufacture frequently demands the inclusion of an inert absorptive grinding aid.

The wettable powder as described above can also be used in the preparation of dusts. While such wettable powders can be used directly in dust form, it is more advantageous to dilute them by blending with the dense dust diluent. In this manner, dispersing agents, corrosion inhibitors, and anti-foam agents may also be found as component of a dust.

Thus, the dust compositions of this invention will comprise from about 0.5 to 20.0 weight percent active ingredient, 5 to 25 weight percent filler, 0 to 1.0 weight percent wetting agent and from about 30 to 90 weight percent dense, free-flowing extender, as these terms are used herein. Such dust formulations can contain, in addition, minor amounts of dispersants, corrosion inhibitors, and anti-foam agents derived from the wettable powders used to make the dust.

EMULSIFIABLE OILS

Emulsifiable oils are usually solutions of active material in non-water miscible solvents together with a surfactant.

For the compounds of this invention, emulsifiable oils can be made by mixing the active ingredient with a solvent and surfactant. Suitable solvents for the compound of this invention are chlorinated solvents, non-water miscible ethers, esters, or ketones alone or in admixture with aromatic hydrocarbons. Suitable surfactants are those ionic or non-ionic agents known to the art as emulsifying agents.

Emulsifying agents most suitable for the emulsifiable oil compositions of this invention are long-chain alkyl or mercaptan polyethoxy alcohols, alkylaryl polyethoxy alcohols, sorbitan fatty acid esters, polyoxyethylene ethers with sorbitan fatty acid ester, polyethylene glycol esters with fatty rosin acids, fatty alkylol amide condensates, calcium and amine salts of fatty alcohol sulfates, oil soluble petroleum sulfonates or, preferably mixtures of these emulsifying agents. Such emulsifying agents will comprise from about 1 to 10 weight percent of the total composition. As described above, however, up to 5 parts of emulsifying agent for each part of active ingredient can be used.

Thus, emulsifiable oil compositions of the present invention will consist of from about 10 to 50 weight percent active ingredient, about 40 to 82 percent solvents, and about 1 to 10 weight percent emulsifier, as these terms are defined and used above.

In some instances, the oil solution may be intended merely for extension with other oils, and in this instance, the emulsifying agent may be omitted and may be replaced by additional solvent.

GRANULES

Granules are physically stable, particulate compositions containing a compound of this invention which adheres to or is distributed through a basic matrix of a coherent, inert carrier with microscopic dimensions. In order to aid leaching of the active ingredient from the granule, a surfactant can be present.

The inert carrier is preferably of mineral origin, and suitable carriers are natural clays, some pyrophyllites and vermiculite. Suitable setting agents are anionic or non-ionic.

For the granule compositions of this invention, most suitable carriers are of two types. The first are porous, absorptive pre-formed granules, such as pre-formed and screened granular attapulgite or heat expanded, granular, screened vermiculite. On either of these, a solution of the active agent can be sprayed and will be absorbed at concentrations up to 25 weight percent of the total weight. The second type are initially powdered kaolin clays, hydrated attapulgite or bentonite clays in the form of sodium, calcium or magnesium bentonites. Water-soluble salts such as sodium salts may also be present to aid in the disintegration of the granules in the presence of moisture. These ingredients are blended with the active components to give mixtures that are granulated, followed by drying to yield formulations with the active component distributed uniformly throughout the mass. Such granules can also be made with 25 to 30 weight percent active component but more frequently a concentration of about 10 weight percent is desired for optimum distribution. The granular compositions of this invention are most useful in a size range of 15–30 mesh.

The most suitable wetting agents for the granular compositions of this invention depend upon the type of granule used. When pre-formed granules are sprayed with active material in liquid form, the most suitable wetting agents are non-ionic, liquid wetters miscible with the solvent. These are more generally known in the art as emulsifiers and comprise alkylaryl polyether alcohols, alkyl polyether alcohols, polyoxyethylene sorbitan fatty acid esters, polyethylene glycol esters with fatty or rosin acids, fatty alkylol amide condensations, oil soluble petroleum or vegetable oil sulfonates, or mixtures of these. Such agents will usually comprise up to about 5 weight percent of the total composition.

When the active ingredient is first mixed with a powdered carrier and subsequently granulated, liquid nonionic wetters can still be used, but is is usually preferable to incorporate at the mixing stage, one of the solid, powdered anionic wetting agents such as those previously listed for the wettable powders. Such agents will comprise about 0 to 2 weight percent of the total composition.

Thus, the preferred granular formulations of this invention comprise about 5 to 30 weight percent active material, about 0 to 5 weight percent wetting agent, and about 65 to 95 percent inert mineral carrier, as these terms are used herein.

What is claimed is:

1. A composition for inhibiting the growth of lepidopterous larvae on plants comprising 1 to 2 parts of *Bacillus thuringiensis* and 1 part of chlordimeform having the structure

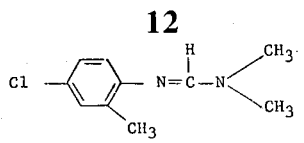

2. The composition according to claim 1, wherein said *Bacillus thurengiensis* and said chlordimeform are included in equal parts in said composition.

3. The composition according to claim 1, wherein said composition includes two parts of *Bacillus thurengiensis* and one part of chlordimeform.

4. A method of controlling the growth of lepidopterous larvae on a plant selected from the group consisting of cole plants, leafy vegetables, tomatoes, cotton, corn, and tobacco, which comprises applying a larvae growth-inhibiting amount of the composition of claim 1 to said plant.

5. The method according to claim 4, wherein said composition includes equal parts of *Bacillus thurengiensis* and chlordimeform.

6. The method according to claim 4, wherein said composition includes two parts of *Bacillus thurengiensis* and one part of chlordimeform.

* * * * *

Disclaimer 3,937,813.—*Robert Kingsbury Clark, Jr.,* St. Petersburg, Fla. INSECTICIDAL COMPOSITIONS COMPRISING MIXTURES OF BACILLUS THURINGIENSIS AND CHLORDIMEFORM. Patent dated Feb. 10, 1976. Disclaimer filed June 26, 1985, by the assignee, *Abbott Laboratories.*

Hereby enters this disclaimer to claims 1-6 of said patent.
[*Official Gazette August 27, 1985.*]